United States Patent [19]

Applegate et al.

[11] Patent Number: 4,988,444
[45] Date of Patent: Jan. 29, 1991

[54] PREVENTION OF BIOFOULING OF REVERSE OSMOSIS MEMBRANES

[75] Inventors: Lynn E. Applegate, Wilmington, Del.; Carl W. Erkenbrecher, Jr., Elkton, Md.; Harvey Winters, Pompton Lakes, N.J.

[73] Assignee: E. I. Du Pont de Nemours and Company, Wilmington, Del.

[21] Appl. No.: 351,238

[22] Filed: May 12, 1989

[51] Int. Cl.$^5$ ................................................. C02F 1/76
[52] U.S. Cl. ..................................... 210/636; 210/639; 210/754; 210/764; 422/29; 422/37
[58] Field of Search ............... 210/636, 639, 764, 754, 210/756, 757, 653; 422/28, 29, 37

[56] References Cited

U.S. PATENT DOCUMENTS

| | | | |
|---|---|---|---|
| 2,061,031 | 11/1936 | Henderson | 210/764 |
| 4,239,622 | 12/1980 | Ridgway | 422/37 |
| 4,278,548 | 7/1981 | Bettinger et al. | 210/636 |
| 4,364,835 | 12/1982 | Cheh | 210/752 |
| 4,711,722 | 12/1987 | Toyoshi et al. | 210/639 |

FOREIGN PATENT DOCUMENTS 6078689 10/1983 Japan ................................. 210/636

OTHER PUBLICATIONS

Charlton and Levine, "The Halogens", p. 402, FIG. 48 (1935).
Ridgeway et al.; Biofilm Fouling of RO Membranes-Its Nature and Effect on Treatment of Water for Reuse--Journal AWWA, Jun. 1984, pp. 94-102.
Applegate et al.; Monitoring and Control of Biological Activity in Permasep® Seawater RO Plants-Elsevier Science Publishers B.V., Desalination, 65 (1987), pp. 331-359.
Pohland et al.—Successful Operation of a Permasep Permeator Reverse-Osmosis System on Biologically Active . . . Water,—Amer. Chem. Society, 1981, pp. 399-406.

Primary Examiner—Peter Hruskoci
Assistant Examiner—Krisanne Shideler
Attorney, Agent, or Firm—Craig H. Evans

[57] ABSTRACT

An improved process is disclosed for killing and inhibiting growth and reproduction (aftergrowth) of microorganisms comprising adding sufficient chloramine to kill the microorganisms without oxidizing high molecular weight organics, which are not easily assimilated by organisms that survive, into lower molecular weight ones, which are easily assimilated.

6 Claims, No Drawings

PREVENTION OF BIOFOULING OF REVERSE OSMOSIS MEMBRANES

FIELD OF INVENTION

This invention relates to a process used to treat raw water, particularly seawater, to prevent biofouling of equipment, particularly reverse osmosis modules containing polyamide membranes.

BACKGROUND OF INVENTION

Hollow-fiber and spiral-wound devices employing membranes such as asymmetric polyamide, thin-film composite and cellulose acetate membranes are used in a wide variety of reverse osmosis (RO) applications. The permselective properties of these membranes permit the purification of liquid streams to eliminate undesirable dissolved components. One significant use of these membranes is desalination of seawater or brackish water.

While currently available reverse osmosis units are highly effective in their intended applications, biological activity present in liquid streams being treated can lead to biofouling, causing poor performance and limiting the life of the unit. Biofouling or clogging of the RO unit results when microorganisms coat or become embedded and multiply on the membranes.

Biological activity is dependent on site-specific factors such as temperature, pH, organic and inorganic nutrients, oxygen availability, sunlight, and pollution and/or surface water run-off. Thus, the concentration and types of microorganisms depend on the source of the water to be treated (raw water) and seasonal conditions. That is, water from seawells has significantly lower biological activity than surface seawater Also, deep surface seawater usually has less activity than shallow shoreline seawater Activity at a single site will increase during summer months.

Ridgway, et al. teach in "Biofilm Fouling of RO Membranes -Its Nature and Effect on Treatment of Water for Reuse", Journal—American Water Works Association. June 1984, pp. 94–102, the effect of chlorine disinfection of raw water from waste treatment to RO units having cellulose acetate membranes. The raw water contained a high concentration of ammonia, typically more than 15 milligrams per liter (mg/L). Effects in RO feedwater containing a low combined chlorine residual (1-3 mg/L) were compared with RO feedwater to which an additional 15-20 mg/L chlorine was added. High concentrations of combined chlorine did not prevent adhesion of bacteria to the surfaces of the membrane, even though, with one unexplained exception, no colonizing microorganisms were recovered from the membrane surfaces exposed to high combined chlorine. Dechlorination prior to passing the feed to the membrane was not employed Applegate et al. teach in "Monitoring and Control of Biological Activity in Permasep® Seawater RO Plants", Desalination, 65 (1987), pp. 331-359, typical pretreatment to control biological activity when feeding seawater to Permasep® RO units which employ polyamide membranes. Chlorination-dechlorination coupled with sodium bisulfite shock treatment is used.

Free chlorine [hypochlorous (HOCl) and hypobromous acid (HOBr)]is taught as the main disinfecting agent. When chlorine is added to seawater, most of the HOCl reacts with the high concentration of bromide ion ($Br^-$) in the seawater to form HOBr. For the sake of simplicity, Applegate et al. use the term "chlorine" to refer to the HOBr with some HOCl that is typically present The same terminology will be used herein in the case of seawater.

Applegate et al. teach that sufficient chlorine as a gas, a solution [NaOCl or $Ca(OCl)_2$] or from an electrolytic chlorine generator must be added to exceed the chlorine demand and, if present, the chlorine breakpoint. The chlorine demand is that needed to quickly chlorinate species such as $Fe^{++}$, $H_2S$, $NO_2^-$, and certain organic compounds. The chlorine breakpoint is the point at which any chloramines (referred to as "combined chlorine") formed due to the presence of ammonia, for example, breakdown and free chlorine residuals begin to form. Dechlorination is taught as necessary since the asymmetric polyamide RO membranes employed are adversely affected (increased salt passage and decreased product flow) by chlorine Sodium metabisulfite ($Na_2S_2O_5$) is the dechlorination agent of choice. $Na_2S_2O_5$ shock treatments (higher concentrations for longer periods) in conjunction with chlorination-dechlorination are also taught.

Pohland et al. teach in "Successful Operation of a Permasep® Permeator Reverse-Osmosis System on Biologically Active Feed Water", American Chemical Society Symposium Series 153, Synthetic Membranes, (1981), pp. 399–406, a method for resolving a biological fouling problem in polyaramide-membrane-equipped RO units by intermittently injecting an excess of a 10 percent solution of potassium iodide (as source of iodine) into the chlorinated feedwater while at the same time discontinuing the flow of sodium metabisulfite.

U.S Pat. No. 4,278,548 teaches a process for inhibiting the growth of microorganisms on polyamide membranes while not seriously damaging the polymeric structure of the membrane. The process introduces an additive into the process stream prior to its entering a RO module containing a semipermeable polyamide membrane for a period of 30 minutes to 3 hours per 72 hours of operation. The additive is selected from the group consisting of iodine, hydrogen peroxide, sodium persulfate, ammonium persulfate and sodium perborate.

Severe microbial fouling of RO membranes in some applications can readily occur even when chlorine is used as a biocide. This is particularly true when dechlorination is necessary such as when polyamide membranes are employed While not wishing to unnecessarily limit the invention, it has now been discovered that, in the case of seawater, this is because the chlorine oxidizes and sufficiently degrades certain organics such as the humic acid materials present in seawater into short-chain organic compounds that surviving microorganisms can use as an energy/carbon food source to rapidly grow and reproduce. With dechlorination, there is no chlorine present to check the growth of the surviving microorganisms. In non-seawater applications containing refractile compounds similar to humic acid, it is likely that the chlorine treatment would also break the compounds into assimilable energy/carbon food sources.

Humic acid material is produced by decay of algae and is generally present in higher concentrations the closer one is to shore. Humic acids are dissolved organics of a polymeric nature. They are high molecular weight compounds containing benzene and aromatic rings. Because of their refractile nature, humic acids are usually not considered to be energy/carbon sources for bacteria. Oxidizing agents such as chlorine have been found to break these compounds into lower molecular weight units which are assimilable organics useful as an energy/carbon source. Thus, the very pretreatment suggested in the art encourages rapid growth and subsequent fouling of equipment, particularly when dechlorination is required such as when the membrane would degrade in the continual presence of chlorine

SUMMARY OF INVENTION

The present invention provides an improved process for killing and inhibiting growth and reproduction (aftergrowth) of microorganisms particularly in circumstances where continual presence of chlorine is not possible as in the case of polyamide membranes which are known to degrade in the presence of chlorine. The process comprises adding sufficient chloramine to the raw water to be treated (or producing it in situ) to destroy the microorganisms. It has been found that the chloramine, unlike chlorine, does not oxidize high molecular weight organics such as humic acid, which are not easily assimilated by organisms that survive, into lower molecular weight ones, which are easily assimilated.

DETAILED DESCRIPTION OF INVENTION

While the present invention has applicability in any equipment susceptible to microbiological fouling, it is particularly applicable in circumstances where dechlorination is required such as in the operation of RO units based on polyamide membranes. Such polyamide membranes can be in the form of flat films or hollow fibers and can be prepared from a variety of polyamides. Representative films and RO devices prepared from films that generally require dechlorination are described in detail in U.S Pat. Nos. 3,567,632; 4,039,440; 4,259,183; 4,277,344; 4,557,949; and 4,529,646 which are incorporated herein by reference.

It has been discovered that microorganisms can be destroyed without generating a food source needed for aftergrowth of any surviving microorganisms by adding a chloramine to the raw water or by forming it in situ by injecting $NH_3$ followed by the addition of chlorine To protect polyamide membranes in RO applications, the feedwater to the membrane is preferably then dechlorinated by use of reducing agents.

$NH_3$ may be added in the form of $NH_3$ gas, $NH_4OH$, $NH_4Cl$, or $(NH_4)_2SO_4$.

Chlorine may be added in any form that forms free chlorine (hypochlorous and hypobromous acid) upon contact with the raw water. Preferred sources of chlorine are chlorine gas, hypochlorites such as $NaOCl$ and $Ca(OCl)_2$, and electrolytically-generated chlorine.

While any reducing agent known in the art may be used, sodium metabisulfite ($Na_2S_2O_5$) is the dechlorination agent of choice. Others include carbon filters, $SO_2$ and sodium thiosulfate.

Preferably, the chloramine is made in situ by first adding $NH_3$ followed by chlorine. If the full amount of chlorine needed to make the chloramine in situ is added first, the $NH_3$ must be added quickly, say in less than 1 minute, to avoid significant degradation of refractile organics by the chlorine.

Chlorine in small amounts (less than about 0.5 mg/L), may be added prior to the $NH_3$, for instance at the raw water intake, to control "macro-biological" growth or buildup of slime in the intake pipeline so long as sufficient chloramine is added or produced in situ shortly thereafter. So long as the amount of chlorine added at the intake for control of macrobiological growth is low enough to avoid excessive degradation of refractile materials such as humic acid, the allowable length of time before chloramine addition can be significantly longer than when the full amount of chlorine is added. The allowable time varies with chlorine concentration and the pH and temperature of the water, the preferable time limit being less than 15 minutes, more preferably no more than 5 minutes. One skilled in the art will be able to determine the allowable time for specific conditions based on experimentation.

The mole ratio of $NH_3$ to chlorine as $HOCl$ should be such that chloramine is the predominant species formed. In seawater, for example $HOCl$ reacts with naturally-occurring $Br^-$ but at a much slower rate than with $NH_3$. If the concentration of $NH_3$ is too low, $HOBr$, which degrades refractile organics, will predominate. The preferred ratio depends primarily on pH at any given raw water temperature. When $NH_3$ is added to seawater, pH will control the concentration of the $NH_3$ based on the following equation:

$$[NH_3] = N_T / (1 + K_b/[OH^-]), \text{ where:}$$

$$N_T = [NH_3] + [NH_4^+] \text{ and } K_b = 1.77 \times 10^{-5}.$$

Thus, for a given pH, the concentration of the $NH_3$ added and the concentration of chlorine used may have to be adjusted to obtain chloramine as the predominant species. When, for example, 10 mg/L of $NH_4Cl$ are added to seawater, the concentration of $NH_3$ will decrease by about 2 logs as the pH decreases from 8.0 to 6.0 thus allowing the slower competing reaction of chlorine with $Br^-$ to predominate. Therefore, at lower pH's sufficiently higher ratios of $NH_3$ to $HOCl$ are required to minimize the competing $HOCl$ reaction with $Br^-$ which forms $HOBr$ which in turn degrades refractile organics into lower molecular weight energy/carbon food sources. For the present process, the pH should be about 6.0 to 8.5, preferably about 6.5 to 8.5. At lower pH's, chloramine will not form or will be converted to free chlorine and, at higher pH's, solid particulate will form and adversely affect operation of most systems or require added filtration to handle.

The mole ratio of $NH_3$ to $HOCl$ should be above 0.5:1, preferably about 2:1 or higher particularly at lower pH's.

The temperature of the raw water or the feedwater to the RO unit is not critical to the process of this invention. It is important, however, since the growth characteristics of microorganisms, the rate of chloramine formation if made in situ, and the rate of refractile organic degradation vary with temperature and, furthermore, there are design temperature limitations on some equipment. At lower temperatures (below about 15° C.), bacterial growth following a typical chlorination-dechlorination in most systems decreases to the point that the treatment of this invention loses some practical importance. Above about 25° C., such aftergrowth increases significantly and the process becomes extremely important, particularly in the case of RO plants where efficiency is greatly affected by biological growth In an RO plant using polyamide membranes, about 40° C. is the upper temperature limit without adversely affecting the membrane. Thus, the typical operating range for the present process will be about 15° to 40° C. and more typically 20° to 35° C.

Sufficient chloramine should be added to the raw water or generated in situ for preferably a 3 log kill (99.9%), more preferably a 4 log kill (99.99%) of the microorganisms that are present. By kill, it is meant that the microorganisms will at least be sufficiently stressed or destroyed that they will not form colonies in 72 hours on plating media.

Since the amount of chloramine needed will vary depending on factors such as temperature, pH, the microorganisms present, and others known to those skilled in the art, the amount to be employed should be determined by measuring the effectiveness in initially killing the microorganisms in a raw water sample. To confirm the adequacy of the amount, samples should be allowed to incubate for about 24 hours and aftergrowth should be measured If aftergrowth is excessive, additional chloramine should be used. By excessive, we mean such aftergrowth as would be predictive of fouling in actual practice to the extent that disinfection and cleaning would be required after an uneconomically short time, say less than weekly. If too little is employed, the effectiveness of the present process will be reduced but will be superior to a process in which refractile organics are degraded to form energy/carbon food sources for the surviving microorganisms. Employing too much chloramine simply creates an economic penalty.

The analytical techniques and data disclosed in the following examples, which are not intended to limit the invention, will provide the guidance that one skilled in the art needs to optimize the concentrations for a given treatment situation.

EXAMPLES

In the following examples chlorine demand free water (CDFW) was prepared according to standard methods as described in "Standard Methods for the Analysis of Water and Wastewater", *American Public Health Association*, 16th Ed., 1985, from reverse osmosis, demineralized, 18 megohm-cm water. ASTM Sea Salts, from Lake Products Co., were then dissolved in the CDFW to make a 35,000 mg/L ASTM artificial seawater, pH was adjusted to the desired pH by the addition of 1N HCl or 1N NaOH as needed, and the seawater was then filter sterilized using a 0.2 micrometer cellulose acetate membrane filter.

Stock solutions of yeast extract [1.0 % (w/v); Difco Co., Detroit, Mich., #0127-02-6] and humic acid [100 mg/L; Aldrich Chemical Co., sodium salt technical #H1,675-2] were prepared and filter sterilized before use.

The bacterial challenge used was prepared by diluting a mixture of eleven bacteria isolated from a Middle East RO facility in either Trypticase ® Soy Broth (BBL) or Marine 2216 Broth (Difco) to about $5 \times 10^5$ CFU/mL. Seven of the bacteria were classified as marine bacteria since they grew on Marine Agar 2216 (MA) but not Trypticase ® Soy Broth Agar (TSBA) and four were classified as terrestrial since they could grow on either MA or TSBA. The bacteria used in the mixture were grown overnight (about 16-24 hours) in either the Marine Broth or Trypticase ® Soy Broth at 23°-28° C.

EXAMPLE 1 (Planktonic Studies)

Five sterile Pyrex ®, low actinic, glass stoppered flasks were filled with 200 milliliters (mL) of the sterile ASTM artificial seawater containing 0.001% (w/v) yeast extract. Additionally, the bacterial challenge (Cells), 5 mg/L sodium hypochlorite (NaOCl), 10 mg/L ammonium chloride (NH4Cl), and 2.5 mg/L humic acid (HA) were added in the order indicated to the flasks:

| FLASK | INGREDIENTS IN ORDER ADDED |
|---|---|
| 1 | CELLS |
| 2 | CELLS + NaOCl |
| 3 | CELLS + NH4Cl + NaOCl |
| 4 | HA + CELLS + NaOCl |
| 5 | HA + CELLS + NH4Cl + NaOCl |

Tests were carried out at the temperatures and pH's indicated in the following tables. At room temperature (25° to 27° C.), the contents in the flasks were stirred with a sterile magnetic stirrer. At 15° and 35° C., the flasks were shaken on a modified Gyrotory Water Bath Shaker coupled to a temperature regulated circulator.

Aliquots were taken aseptically from each of the five flasks 15 minutes (min.) after addition of all the ingredients. The aliquots were analyzed for bacteria by a modified standard serial dilution spread plating technique (*Standard Methods*). For aliquots taken from flasks containing chlorine or chloramine the samples were neutralized with $Na_2S_2O_5$ prior to plating onto Trypticase ® Soy Broth Agar (TSBA) or Marine Agar 2216 (MA). TSBA plates were counted after 48 hours and MA plates were counted after 72 hours of incubation at 25° C. to determine the number of colony forming units per milliliter (CFU/mL). Results are reported in Table I. For TSBA media, the cells were those classified as terrestial. For MA media, all eleven isolates were included.

After 30 min., the total chlorine in flasks 2 to 5 was neutralized with 10 mg/L $Na_2S_2O_5$. The flask contents were then allowed to incubate for an additional 24 hours to determine aftergrowth. Aliquots were again taken and analyzed for bacteria in the same manner as above. Results are reported in Table II. The pH reported in Table II is lower than that in Table I because the $Na_2S_2O_5$ addition reduced the pH. pH was measured with a Beckman pH meter equipped with a combination electrode and an automatic temperature compensating probe.

TABLE I

BIOCIDAL ACTIVITY OF CHLORAMINE AND CHLORINE

| pH | Temp. °C. | Media[b] | Initial CFU ($\times 10^1$)/mL | CFU ($\times 10^1$)/mL After 15 Minutes[a] | | | |
|---|---|---|---|---|---|---|---|
| | | | | F2 | F3 | F4 | F5 |
| 6.3 | 15 | TSBA | 32,000 | ND[c] | ND | 12 | ND |
| | | MA | 32,000 | 11 | ND | 68 | ND |
| 6.0 | 25 | TSBA | 8,200 | ND | ND | ND | 1 |
| | | MA | 12,000 | 34 | ND | 76 | ND |
| 6.7 | 35 | TSBA | 16,000 | ND | ND | 1 | ND |
| | | MA | 31,000 | ND | ND | ND | ND |
| 7.5 | 15 | TSBA | 16,000 | 44 | ND | 3 | 3 |
| | | MA | 31,000 | 82 | ND | 20 | 6 |
| 7.4 | 27 | TSBA | 30,000 | ND | ND | 8 | ND |
| | | MA | 31,000 | ND | ND | 200 | ND |
| 7.0 | 35 | TSBA | 36,000 | 2 | ND | ND | ND |
| | | MA | 62,000 | 3 | ND | 9 | 1 |
| 8.4 | 15 | TSBA | 32,000 | 65 | ND | 6 | ND |
| | | MA | 27,000 | 61 | ND | 10 | ND |
| 8.0 | 25 | TSBA | 58,000 | ND | ND | 5 | ND |
| | | MA | 100,000 | ND | ND | 7 | ND |
| 8.0 | 35 | TSBA | 120,000 | ND | ND | ND | ND |

TABLE I-continued

BIOCIDAL ACTIVITY OF CHLORAMINE AND CHLORINE

| | Temp. | | Initial | CFU ($\times 10^1$)/mL After 15 Minutes[a] | | | |
|---|---|---|---|---|---|---|---|
| pH | °C. | Media[b] | CFU ($\times 10^1$)/mL | F2 | F3 | F4 | F5 |
| | | MA | 170,000 | ND | ND | ND | ND |

[a] Limit of Detection = $1 \times 10^1$ CFU/mL
[b] TSBA = Trypticase ® Soy Broth Agar
MA = Marine Agar 2216
[c] ND = Non-detectable

TABLE II

BACTERIAL AFTERGROWTH IN CHLORAMINE AND CHLORINE SYSTEMS

| | Temp. | | | CFU ($\times 10^1$)/mL After 24 Hours[a] | | | |
|---|---|---|---|---|---|---|---|
| pH | °C. | Media[b] | F2 | F3 | F4 | F5 | |
| 6.1 | 15 | TSBA | ND[c] | ND | 11 | ND | |
| | | MA | 2 | ND | 3 | ND | |
| 5.3 | 25 | TSBA | ND | ND | ND | 1 | |
| | | MA | ND | ND | ND | ND | |
| 5.7 | 35 | TSBA | 190 | ND | ND | ND | |
| | | MA | 220 | ND | 1 | ND | |
| 7.3 | 15 | TSBA | 600 | 70 | 41 | 7 | |
| | | MA | 3,000 | 75 | 3,100 | 550 | |
| 7.1 | 27 | TSBA | 16,000 | ND | 280,000 | ND | |
| | | MA | 3,100,000 | ND | 2,300,000 | ND | |
| 6.7 | 35 | TSBA | 930,000 | 60,000 | 210,000 | ND | |
| | | MA | 500,000 | 1,700 | 210,000 | ND | |
| 8.2 | 15 | TSBA | 25 | ND | 74 | 62 | |
| | | MA | 540 | 7 | 45 | 30 | |
| 7.6 | 25 | TSBA | 100,000 | ND | 140,000 | ND | |
| | | MA | 420,000 | ND | 650,000 | ND | |
| 7.6 | 35 | TSBA | 50,000 | 460,000 | 950,000 | 610,000 | |
| | | MA | 60,000 | 510,000 | 1,300,000 | 580,000 | |

[a] Limit of Detection = $1 \times 10^1$ CFU/mL
[b] TSBA = Trypticase ® Soy Broth Agar
MA = Marine Agar 2216
[c] ND = Non-detectable

EXAMPLE 2 (Planktonic Studies)

Example 1 at a starting pH of 8.0 and temperature of 35° C. after $Na_2S_2O_5$ addition after 30 minutes) was repeated using a higher biocide dosage (6mg/L HOCl for F2 and F4; 12 mg/L $NH_4Cl$ + 6 mg/L HOCl for F3 and F5). Results in Table III indicate extensive aftergrowth when humic acid is present in a chlorine system (F4) but not when humic acid is present in a chloramine system (F5). The correct dosage of biocide needed to effectively kill the microorganisms and prevent aftergrowth depends on site-specific factors such as temperature and pH.

TABLE III

BACTERIAL AFTERGROWTH IN CHLORAMINE AND CHLORINE SYSTEMS AT HIGHER BIOCIDE DOSAGE

| | Temp. | | CFU ($\times 10^1$)/mL After 24 Hours[a] | | | |
|---|---|---|---|---|---|---|
| pH | °C. | Media[b] | F2 | F3 | F4 | F5 |
| 8.0 | 35 | TSBA | ND[c] | ND | 35,000 | ND |
| | | MA | ND | ND | 200,000 | ND |

[a] Limit of Detection = $1 \times 10^1$ CFU/mL
[b] TSBA = Trypticase ® Soy Broth Agar
MA = Marine Agar 2216
[c] ND = Non-detectable

EXAMPLE 3 (Planktonic Studies)

Example 1 at starting pH 8.0 at 25° C. (pH 7.6 at 25° C. after $Na_2S_2O_5$ addition) was again repeated except that the inoculum containing the bacteria was first centrifuged to separate the bacteria from the broth, which was discarded. The bacteria were then added to sterilized ASTM seawater and then separated by centrifugation. The procedure was repeated twice before adding the bacteria to the flasks. As can be seen from the results in Table IV, aftergrowth did not occur in either the chlorine or chloramine system in the absence of humic acid (F2 and F3) or in the chloramine system in the presence of humic acid (F5). This can be contrasted with the data in Table II, in which aftergrowth in the chlorine system was comparable regardless of humic acid. Apparently the TSBA or MA added along with the cells in Example 1 were degraded to an acceptable energy/carbon food source by the chlorine.

TABLE IV

BACTERIAL AFTERGROWTH WITH WASHED BACTERIA IN CHLORINE AND CHLORINE SYSTEMS

| | Temp. | | CFU ($\times 10^1$)/mL After 24 Hours[a] | | | |
|---|---|---|---|---|---|---|
| pH | °C. | Media[b] | F2 | F3 | F4 | F5 |
| 8.0 | 25 | TSBA | 1 | ND[c] | 38 | 1 |
| | | MA | 11 | ND | 15,000 | ND |

[a] Limit of Detection = $1 \times 10^1$ CFU/mL
[b] TSBA = Trypticase ® Soy Broth Agar
MA = Marine Agar 2216
[c] ND = Non-detectable

EXAMPLE 4 (Periphytic Studies)

The same bacterial isolated from the Middle East RO facility as described above in the Planktonic Examples were maintained on Marine Agar 2216 (Difco, Detroit, Mich.). An 18-hour agar culture of each isolate was grown at 27° C. and was used to prepare a light suspension in sterile ASTM seawater. The number of bacteria per milliliter was determined with a Petroff-Hauser counting chamber and diluted to a final concentration of $1-2 \times 10^7$ cells/mL. Then, 1.0 mL of the suspension was inoculated into five flasks each containing 100 mL. sterile ASTM seawater with 0.001% yeast extract. In addition, the five flasks contained HOCl, $NH_4Cl$, and Humic Acid (HA) added as follows:

| FLASK | INGREDIENTS IN ORDER ADDED |
|---|---|
| 1 | (control) |
| 2 | 5 mg/L HOCl |
| 3 | 10 mg/L $NH_4Cl$ + 5 mg/L NaOCl |
| 4 | 2.5 mg/L HA + 5 mg/L HOCl |
| 5 | 2.5 mg/L HA + 10 mg/L $NH_4Cl$ + 5 mg/L NaOCl |

The inoculated medium was poured into sterile incubated at the temperatures indicated in Table IV. Slides were removed at designated times, rinsed with sterile ASTM seawater, and fixed in 1.0 % (v/v) acetic acid. The slides were then rinsed with distilled water, stained for two minutes with 1.0 % (w/v) crystal violet, and then rinsed thoroughly with distilled water.

The mean number of cells per microscopic field was calculated based on counts made of ten microscopic fields using an American Optical binocular phase contrast microscope. Cell density was determined by computing the number of cells per square centimeter (cells/$cm^2$) of glass slide surface.

As can be seen from Table V, the bacteria generally showed greater attachment in the case of chlorine when humic acid was present (F4) than when the humic acid was not present (F2). On the other hand, the attachment after 96–123 hours in the chloramine cases was always significantly less than in the corresponding chlorine cases and did not show any significant increase when humic acid was present (F5) than when it was not (F3).

TABLE V

Periphytic Attachment for Chlorine and Chloramine Processes

| pH | Temp. °C. | Time Slide Exposed (HR.) | Microscopic Count/cm² (× 10³) | | | | |
|---|---|---|---|---|---|---|---|
| | | | F1 | F2 | F3 | F4 | F5 |
| 8.0 | 18 | 20 | 310 | 7 | 0 | 19 | 1 |
| | | 48 | 6,900 | 4 | 0 | 828 | 2 |
| | | 96 | 4,200 | 800 | 3 | 1,900 | 31 |
| 8.0 | 25 | 21 | 370 | 0 | 0 | 650 | 0 |
| | | 40 | 5,000 | 41 | 0 | 500 | 37 |
| | | 96 | 3,300 | 510 | 0 | 6,000 | 43 |
| 8.0 | 35 | 24 | 230 | 0 | 0 | 7 | 0 |
| | | 44 | 350 | 2 | 0 | 90 | 0 |
| | | 96 | 5,400 | 610 | 0 | 820 | 0 |
| 7.0 | 18 | 24 | 78 | 1 | 0 | 0 | 0 |
| | | 48 | 890 | 93 | 6 | 41 | 0 |
| | | 96 | 3,800 | 2,700 | 480 | 83,000 | 41 |
| 7.0 | 25 | 21 | 1,500 | 4 | 0 | 39 | 0 |
| | | 40 | 2,300 | 12 | 3 | 76 | 0 |
| | | 123 | 4,800 | 3,900 | 58 | 8,800 | 14 |
| 7.0 | 35 | 21 | 370 | 5 | 0 | 61 | 0 |
| | | 40 | 1,500 | 18 | 0 | 2,900 | 0 |
| | | 123 | 3,500 | 5,900 | 61 | 22,000 | 10 |
| 5.9 | 19 | 22 | 33 | 0 | 0 | 1 | 0 |
| | | 40 | 510 | 3 | 0 | 66 | 0 |
| | | 96 | 7,800 | 590 | 3 | 8,300 | 0 |
| 6.2 | 25 | 20 | 670 | 3 | 0 | 1 | 3 |
| | | 46 | 4,900 | 600 | 1 | 33 | 4 |
| | | 96 | 9,700 | 8,300 | 55 | 440 | 21 |
| 6.2 | 35 | 20 | 200 | 9 | 0 | 1 | 1 |
| | | 46 | 8100 | 780 | 2 | 50 | 4 |
| | | 96 | 14,000 | 11,000 | 71 | 3,900 | 260 |

EXAMPLE 5 (Periphytic Studies)

Example 4 at starting pH of 8.0 and temperatures of 25° and 35° C. were repeated except the bacteria were first centrifuged from the broth and washed in sterile seawater as in Example 3. The results reflected in Table IV show significant aftergrowth and periphytic attachment when humic acid is exposed to chlorine (F4), but not in the other cases.

TABLE VI

Periphytic Attachment for Chlorine and Chloramine Processes Using Washed Bacteria

| pH | Temp. °C. | Time Slide Exposed (HR.) | Microscopic Count/cm² (× 10³) | | | | |
|---|---|---|---|---|---|---|---|
| | | | F1 | F2 | F3 | F4 | F5 |
| 8.0 | 25 | 18 | 71 | 0 | 0 | 6,400 | 0 |
| | | 48 | 17 | 0 | 0 | 43,000 | 0 |
| | | 96 | 41 | 0 | 0 | 51,000 | 0 |
| 8.0 | 35 | 22 | 71 | 0 | 0 | 13 | 0 |
| | | 48 | 894 | 0 | 0 | 850 | 0 |
| | | 96 | 3,500 | 1 | 0 | 51,000 | 9 |

We claim:

1. A process for preventing aftergrowth of microorganisms and the biofouling of equipment which equipment is adversely affected by chlorine, the equipment being fed by a liquid process feed stream containing chlorine degradable organic material that, when in degraded form, provides an energy/carbon food source that is assimilable by microorganisms and that, in the absence of chlorine, enables microorganisms to grow and reproduce comprising adding into the process feed stream an amount of a chloramine sufficient to kill at least 99 percent of microorganisms present and then dechloraminating prior to the process stream's entering the equipment.

2. The process of claim 1 wherein the chloramine is made in situ by injecting $NH_3$ and chlorine in a means that produces chloramine before the chlorine degradable organic material is sufficiently degraded to provide an energy/carbon food source that is assimilable by any surviving microorganisms and that enables the surviving microorganisms to grow and reproduce after dechlorination.

3. The process of claim 1 wherein the amount of chloramine is an amount sufficient to kill at least 99 percent of the microorganisms present in the liquid process stream.

4. In the process for continuously purifying a liquid process stream by passing it through at least one reverse osmosis module comprising a core member having a semipermeable membrane positioned in a manner whereby the liquid permeates through the membrane producing flows of permeate and concentrate, the improvement which comprises inhibiting the growth of microorganisms in said liquid process stream and on the membrane by continuously adding into the process stream an amount of a chloramine sufficient to kill at least 99 percent of the microorganisms in the stream followed by adding sufficient reducing agent to dechloraminate prior to the process stream's entering the reverse osmosis module.

5. The process of claim 4 wherein the chloramine is made in situ by injecting $NH_3$ and chlorine in a means that produces chloramine before the chlorine degradable organic material is sufficiently degraded to provide an energy/carbon food source that is assimilable by any surviving microorganisms and that enables the surviving microorganisms to grow and reproduce after dechlorination.

6. The process of claim 4 wherein the membrane is a polyamide membrane.

* * * * *

UNITED STATES PATENT AND TRADEMARK OFFICE
CERTIFICATE OF CORRECTION

PATENT NO. : 4,988,444

DATED : Jan. 29, 1991

INVENTOR(S) : Applegate et al.

It is certified that error appears in the above-identified patent and that said Letters Patent is hereby corrected as shown below:

Column 10, line 32, replace "99" with --99.9--.

Signed and Sealed this

Ninth Day of June, 1992

Attest:

DOUGLAS B. COMER

*Attesting Officer*  Acting Commissioner of Patents and Trademarks